United States Patent [19]

Willms et al.

[11] 4,440,565
[45] Apr. 3, 1984

[54] HETEROCYCLICALLY SUBSTITUTED (HALOGENO)ALKYL- AND (HALOGENO)ALKOXYSULFONYLUREAS, AND THEIR USE IN AGRICULTURE

[75] Inventors: Lothar Willms, Unkel; Hilmar Mildenberger; Dieter Günther, both of Kelkheim; Klaus Bauer, Rodgau; Helmut Bürstell, Frankfurt am Main; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 360,489

[22] Filed: Mar. 22, 1982

[30] Foreign Application Priority Data

Mar. 24, 1981 [DE] Fed. Rep. of Germany ....... 3111451

[51] Int. Cl.³ ................. C07D 251/46; C07D 251/52; A01N 43/66; A01N 43/70
[52] U.S. Cl. ..................................... 71/93; 544/199; 544/210; 544/205; 544/213
[58] Field of Search ............... 544/194, 213, 204, 210, 544/199, 196, 205; 71/93

[56] References Cited

U.S. PATENT DOCUMENTS 4,191,553 3/1980 Reap ................................. 544/211
4,238,621 12/1980 Levitt ................................... 71/93

FOREIGN PATENT DOCUMENTS 51466 5/1982 European Pat. Off. .
3111451 10/1982 Fed. Rep. of Germany .

*Primary Examiner*—John M. Ford
*Attorney, Agent, or Firm*—Curtis, Morris & Safford

[57] ABSTRACT

Compounds of the formula

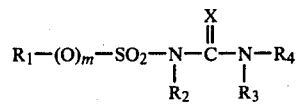

wherein $R_1$ denotes an aliphatic radical which is optionally substituted by halogen and/or interrupted by oxygen, $R_2$ and $R_3$ denote H or alkyl, X denotes oxygen or sulfur, m denotes 0 or 1, and $R_4$ denotes an optionally substituted six-membered heterocyclic ring having 2–3 N atoms, are effective herbicides and growth regulators.

13 Claims, No Drawings

HETEROCYCLICALLY SUBSTITUTED (HALOGENO)ALKYL- AND (HALOGENO)ALKOXYSULFONYLUREAS, AND THEIR USE IN AGRICULTURE

It has already been disclosed that heterocyclically substituted phenylsulfonylureas, such as, for example, N-(4-chloro-6-i-propylamino-1,3,5-triazin-2-yl)-N-i-propyl-N'-(4-chlorophenylsulfonyl)-urea, have herbicidal or plant growth-regulating properties (cf. Dutch Pat. No. 121,788, German Offenlegungsschrift No. 2,715,786 and European Pat. Nos. 1,485, 1,514, 1,515, 4,163, 7,687, 9,419 and 10,560).

It has now been found that heterocyclically substituted (halogeno)alkyl- or (halogeno)alkoxysulfonylureas are also suitable as herbicides and plant growth regulators.

Accordingly, the present invention relates to compounds of the formula I

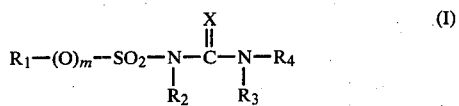

wherein $R_1$ denotes a saturated or unsaturated, branched or straight-chain aliphatic radical which has up to 10 C atoms, is optionally substituted by up to 6 halogen atoms, and, if appropriate, can be interrupted by oxygen, $R_2$ and $R_3$ denote H or $(C_1-C_4)$-alkyl, X denotes O or S, m denotes 0 or 1, $R_4$ denotes a six-membered heterocyclic ring which contains 2-3 nitrogen atoms and is optionally monosubstituted to trisubstituted by halogen, $NO_2$, CN, CHO, $(C_1-C_4)$-alkylamino, $(C_1-C_4)$-dialkylamino, a $(C_1-C_4)$-alkyl radical (which is optionally substituted by halogen, $(C_1-C_3)$-alkoxy, $(C_1-C_3)$-alkylthio, $(C_1-C_3)$-alkylamino, $(C_1-C_3)$-dialkylamino or $(C_1-C_4)$-alkoxycarbonyl), a $(C_1-C_4)$-alkoxy or $(C_1-C_4)$-alkylthio radical (which are optionally substituted by halogen or $(C_1-C_4)$-alkoxycarbonyl), or $(C_1-C_4)$-alkoxycarbonyl, and, if $R_2$ denotes hydrogen, their physiologically tolerated salts with bases.

Aliphatic radicals in the $R_1$ position are to be understood as meaning alkyl radicals, alkenyl radicals having a single or conjugated double bond, or alkynyl radicals. Halogen preferably denotes fluorine, chlorine or bromine. Radicals having at least 3 C atoms are distinguished by a particularly powerful herbicidal action.

The following compounds may be mentioned as examples of heterocyclically substituted sulfonylureas, according to the invention, of the formula I: N-(4-methoxy-6-methyl-pyrimidin-2-yl)-N'-(2,2,2-trichloroeth-1-oxysulfonyl)-urea; N-(4-methoxy-6-methyl-1,3,5-triazin-2-yl)-N'-(2,2,2-trifluoroeth-1-oxysulfonyl)-urea; N-(2,6-dimethyl-5-chloro-pyrimidin-4-yl)-N'-(methoxysulfonyl)-urea; N-(4-methyl-5-ethoxycarbonyl-pyrimidin-2-yl)-N'-(isobutyloxysulfonyl)-urea; N-(4-methoxy-6-methylthiopyrimidin-2-yl)-N'-(2-chloroeth-1-yl-sulfonyl)-urea; N-(4,6-dichloro-pyrimidin-2-yl)-N'-(2-chloroeth-1-yl-sulfonyl)-urea; N-(4-methyl-6-methylthio-1,3,5-triazin-2-yl)-N'-(1,2-dichloro-n-prop-1-yl-sulfonyl)-urea; N-(4-methyl-6-dimethylamino-1,3,5-triazin-2-yl)-N'-(1,2-dichloro-n-prop-1-yl-sulfonyl)-urea; N-(4-methoxy-6-methyl-1,3,5-triazin-2-yl)-N'-(1-methyl-2-chloro-n-prop-1-yl-sulfonyl)urea; N-(4-methoxy-6-methyl-pyrimidin-2-yl)-N'-(2-chloro-3-methoxy-n-prop-1-yl-sulfonyl)-urea; N-(5,6-dimethyl-1,2,4-triazin-3-yl)-N'-(1,2,2-trichloro-eth-1-yl-sulfonyl)urea; N-(4,6-dimethoxy-5-chloro-pyrimidin-2-yl)-N'-(2-chloro-n-but-1-yl-sulfonyl)-urea; N-(4,6-dimethyl-5-nitropyrimidin-2-yl)-N'-(2,4,6,6-tetrachloro-n-hex-1-yl-sulfonyl)-urea; N-(4,5-dimethyl-6-methoxy-pyrimidin-2-yl)-N'-(2-chloro-n-hex-1-yl-sulfonyl)-urea; N-(4-methyl-6-diethylamino-1,3,5-triazin-2-yl)-N'-(vinylsulfonyl)-urea; N-(4,6-dimethyl-5-bromo-pyrimidin-2-yl)-N'-(prop-1-en-1-yl-sulfonyl)-urea; N-(4-methyl-5-nitro-6-chloro-pyrimidin-2-yl)-N'-(3-chloro-prop-1-en-1-yl-sulfonyl)-urea; N-(4-methyl-6-ethoxymethyl-pyrimidin-2-yl)-N'-(4,4-dichlorobut-1-en-1-yl-sulfonyl)-urea; N-(4,6-dimethoxy-1,3,5-triazin-2-yl)-N-methyl-N-(2-chlorovinylsulfonyl)-urea; N-(4,6-diethyl-pyrimidin-2-yl)-N'-(prop-1-en-1-yl-sulfonyl)-urea and the sodium salt thereof; N-(pyrimidin-2-yl)-N'-(prop-1-en-1-yl-sulfonyl)-thiourea; N-(4-chloro-6-isopropylamino-1,3,5-triazin-2-yl)-N-isopropyl-N'-(prop-1-en-1-yl-sulfonyl)-urea; N-(5,6-dimethoxy-1,2,4-triazin-3-yl)-N'-(n-prop-1-oxysulfonyl)-urea; N-(4,6-dimethoxy-5-fluoro-pyrimidin-2-yl)-N'-(n-hept-1-yl-oxysulfonyl)-urea; N-(4,6-dimethyl-5-iodo-pyrimidin-2-yl)-N'-(2-methoxyethoxysulfonyl)-urea; N-(4,6-dichloro-5-(2-chloroethyl)-pyrimidin-2-yl)-N'-(1,3-dichloro-isoprop-2-yl-oxysulfonyl)urea; N-(4-methoxy-5-nitro-6-methyl-pyrimidin-2-yl)-N'-(1,1,1,3,3,3-hexachloro-isoprop-2-yl-oxysulfonyl)-urea; N-(4-trifluoromethyl-6-methyl-pyrimidin-2-yl)-N'-(2,2-dichloro-ethyl-sulfonyl)-urea; N-(4,5-dimethyl-6-methoxyethoxy-pyrimidin-2-yl)-N'-(1,2-dichloro-ethyl-sulfonyl)urea; N-(4-methoxymethyl-5-methyl-6-ethoxy-pyrimidin-2-yl)-N'-(2,3-dichloro-n-prop-1-yl-sulfonyl)-urea; N-(4-(1-ethoxycarbonyl-ethoxy)-6-methyl-pyrimidin-2-yl)-N'-(1,2-dibromo-n-prop-1-yl-sulfonyl)-urea; N-(4-methoxycarbonylmethoxy)-6-methyl-1,3,5-triazin-2-yl)-N'-(2-chloro-n-pent-1-yl-sulfonyl)-urea; N-(4,6-diethylmercapto-pyrimidin-2-yl)-N'-(2-chloro-2-trifluoromethyl-eth-1-yl-sulfonyl)urea; N-(4-methyl-6-(2-bromoethoxy)-pyrimidin-2-yl)-N'-(2,3,4-trichloro-n-but-1-yl-sulfonyl)-urea; N-(4-methoxy-6-methyl-1,3,5-triazin-2-yl)-N'-(3-chloro-2-chloromethylprop-1-yl-sulfonyl)-urea; N-(4,6-dimethyl-mercapto-1,3,5-triazin-2-yl)-N'-(2-chloro-2-chloromethyl-prop-1-yl-sulfonyl)-urea; N-(4-methyl-pyrimidin-2-yl)-N'-(2,3-dichloro-n-but-1-ylsulfonyl)-urea; N-(4-methoxy-5-n-butyl-6-methyl-pyrimidin-2-yl)-N'-(3-chloro-n-but-1-en-1-yl-sulfonyl)-urea; N-(4,6-dimethoxy-1,3,5-triazin-2-yl)-N'-(1-methyl-2,3-dichloro-n-prop-1-yl-sulfonyl)-urea; N-(2,6-dimethyl-pyrimidin-4-yl)-N'-(2-chloro-3-bromo-n-but-1-ylsulfonyl)-urea; N-(5,6-dimethyl-1,2,4-triazin-2-yl)-N'-(1-methyl-n-prop-1-en-1-yl-sulfonyl)-urea and N-(5-chloropyrimidin-2-yl)-N'-(2-chloro-2,4-dibromo-n-but-1-yl-sulfonyl)-urea.

The new compounds of the general formula I can be synthesized from starting materials which are known per se or which are prepared by known processes. The preparation processes comprise reacting (a) compounds of the formula

or

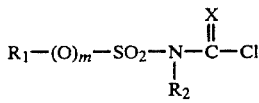 (III)

with compounds of the formula

 (IV)

or (b) compounds of the formula

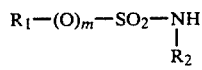 (V)

with compounds of the formula

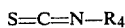 (VI)

or

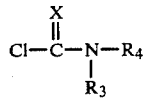 (VII)

wherein, in formula VII, $R_3$ represents $(C_1-C_4)$-alkyl, and, if desired, converting the resulting compounds of the formula I into other compounds of the formula I by splitting off hydrogen halide, addition of halogen at existing multiple bonds, alkylation in the $R_2$ position or salt formation.

Re (a) The reaction of the compounds II or III with IV is preferably effected in inert aprotic solvents, such as, for example, acetonitrile, dichloromethane, toluene, tetrahydrofuran or dioxane, at temperatures between 0° C. and the boiling point of the solvents. When starting materials of the formula III are used, the reaction is carried out in the presence of an acid acceptor, such as, for example, potassium carbonate, pyridine or triethylamine.

Re (b) The reaction of compound V with VI or VII is also preferably carried out in the abovementioned inert solvents, with the addition of basic compounds, such as, for example, potassium carbonate, pyridine or triethylamine, at temperatures between 0° C. and the boiling point of the solvent.

Hydrogen halide (HCl or HBr) is subsequently split off from halogen-containing radicals $R_1$ in a known manner, for example using an alkali metal alcoholate, alcoholic sodium hydroxide solution or potassium hydroxide solution, triethylamine or other acid-eliminating agents, if appropriate in the presence of a further inert solvent or diluent (for example toluene), at temperatures between room temperature and the boiling point.

Addition of halogen ($Cl_2$ or $Br_2$) or hydrogen halide can be effected, in a manner which is also known, at existing or subsequently formed multiple bonds in the $R_1$ position, and new compounds of the formula I can thus be obtained, if desired. The bromination or chlorination is carried out in inert organic solvents, such as, for example, dichloromethane or chloroform, under irradiation, for example with ultraviolet light, or in the presence of compounds, for example azodiisobutyronitrile, which dissociate to give free radicals, at temperatures between 0° C. and the boiling point of the solvent. The addition of hydrogen halide proceeds in the presence of inert solvents (for example toluene), using gaseous HCl or HBr at low temperatures, if appropriate in the presence of a peroxide catalyst.

For subsequent alkylation in the $R_2$ position, the reaction is preferably carried out in inert aprotic solvents, such as, for example, dioxane or dimethylformamide, with the addition of an inorganic base, for example sodium hydride or potassium carbonate, at temperatures from 20° C. to the boiling point of the solvent. Dimethyl sulfate, methyl iodide or ethyl bromide, for example, is employed as the alkylating agent.

Compounds of the formula I in which $R_2$ denotes hydrogen can form salts in which H is replaced by a cation suitable for use in agriculture. These salts are in general metal, ammonium or organic amine salts and are preferably prepared in inert solvents, such as, for example, water, methanol or acetone, at temperatures of 20°–100° C. Examples of suitable bases for the preparation of the salts according to the invention are potassium carbonate, ammonia or ethanolamine.

The starting materials of the formula IV are known or can be prepared according to processes which are known in principle, for example by cyclization of appropriate guanidine derivatives with appropriately substituted 1,3-diketones (cf., for example, "The Chemistry of Heterocyclic Compounds", Vol. XVI (1962) and Supplement I (1970)), or by derivatization of cyanuric chloride (cf., for example, "The Chemistry of Heterocyclic Compounds", L. Rapoport: "s-Triazines and Derivatives" (1959)).

The majority of the sulfonylisocyanates of the formula II are also known, or they can be prepared in a simple manner according to processes which are known in principle (cf. German Auslegeschriften Nos. 1,211,165, 1,226,565, 1,230,016 and 1,568,640, and Chem. Ber. 105, 2791 and 2800 (1972)).

The sulfonylcarbamoyl or -thiocarbamoyl chlorides of the formula III can be prepared according to customary methods, by reacting the alkali metal salts of the corresponding sulfonamides of the formula V, which are known from the literature, with phosgene or thiophosgene.

The isothiocyanates of the formula VI which are required for the reactions according to (b) are known, or are obtainable according to known processes (cf. Tetrahedron 29, 691 (1973); and Japan Kokai No. Sho-51-143686).

The same applies to the heterocyclic carbamoyl chlorides and thiocarbamoyl chlorides of the formula VII (cf., for example, German Auslegeschriften Nos. 1,149,718 and 2,238,870).

Sulfonylureas of the general formula I which contain one or more asymmetric carbon atoms in the aliphatic radical $R_1$ are present in enantiomeric or diastereomeric forms. In general, the corresponding compounds according to the invention are obtained as racemates or as diastereomer mixtures. If desired, the customary techniques can be used to separate these mixtures into the sterically uniform constituents. The compounds mentioned can also be prepared in pure form by using sterically uniform starting materials. If, for example, amino-heterocyclic compounds of the general formula IV are reacted with threo- or erythro-1,2-dichloropropylsulfonyl isocyanate, the corresponding threo- or erythro-1,2- dichloropropylsulfonylureas are obtained. Furthermore, sulfonylureas of the general formula I which contain one or more double bonds in the aliphatic radical $R_1$ can occur as E isomers or as Z isomers in appropriate olefinic substitution, and their preparation in pure form or separation is also possible. If, for example, unsaturated sulfonyl isocyanates of the general formula II are employed as E isomers or as Z isomers, the unsaturated sulfonylureas of the formula I are obtained in sterically uniform form.

The compounds according to the invention exhibit an excellent herbicidal action, and a very good selectivity in important large-scale crops, and are therefore suitable for selectively combating a large number of dicotyledonous and graminaceous, annual and perennial weeds in agriculturally important crops, such as, for example, wheat, barley, rye, rice and maize, sugar beet, soybean and cotton, by the pre-sowing method, pre-emergence method and post-emergence method.

If the compounds according to the invention are applied to the soil surface by the pre-sowing method or pre-emergence method before germination of the weeds, the emergence of the seedlings is not prevented. The weeds grown until the cotyledon stage, but then cease to grow and finally die completely after a few weeks. When the active compounds are applied to the green parts of plants by the post-emergence method, a drastic cessation of growth also occurs very rapidly after treatment, and the weeds remain at the stage of growth existing at the time of application or die completely after a certain time, so that competition from the weeds which is damaging to the crop plants can be eliminated at a very early stage and for a protracted period in this manner.

In addition, the substances according to the invention exhibit outstanding growth-regulating properties in crop plants. They intervene to regulate the plant metabolism and can thus be employed for selectively influencing plant constituents and for facilitating harvesting, for example by initiating desiccation and stunting of growth. Furthermore, they are also suitable for generally controlling and inhibiting undesired vegetative growth, without killing the plants in the process. Inhibition of vegetative growth is very important in the case of many monocotyledonous and dicotyledonous crops, since lodging can be reduced or completely prevented by this means.

The invention therefore also relates to herbicidal or growth-regulating agents which contain a compound of the formula I in combination with customary formulation auxiliaries and inert substances, and their use in the agricultural sector.

The agents according to the invention contain the active ingredients of the formula I in general in an amount of 2–95% by weight. They can be used in the customary preparation, as wettable powders, emulsifiable concentrates, spraying solutions, dusting agents or granules.

Wettable powders are preparations which are uniformly dispersible in water and which also contain, in addition to the active ingredient and in addition to a diluent or inert substance, wetting agents, for example polyoxyethylated alkylphenols, polyoxyethylated fatty alcohols, or alkyl or alkylphenyl sulfonates, and dispersing agents, for example sodium ligninsulfonate, sodium 2,2'-dinaphthylmethane-6,6'-disulfonate, sodium dibutylnaphthalenesulfonate or sodium oleylmethyltaurate.

Emulsifiable concentrates are prepared by dissolving the active ingredient in an organic solvent, for example butanol, cyclohexanone, dimethylformamide, xylene or relatively high-boiling aromatic compounds or hydrocarbons, with the addition of one or more emulsifiers. For example, the following compounds can be used as emulsifiers: calcium alkylarylsulfonates, such as Ca dodecylbenzosulfonate, or non-ionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyethers, sorbitane fatty acid esters, polyoxyethylene sorbitane fatty acid esters or polyoxyethylene sorbitane esters.

Dusting agents are obtained by grinding the active ingredient with finely divided solid substances, for example talc, natural clays, such as kaolin, bentonite or pyrophillite, or diatomaceous earth.

Granules can be prepared either by spraying the active ingredient onto adsorptive, granulated inert material or by the application of active ingredient concentrates by means of adhesives, for example polyvinyl alcohol, sodium polyacrylate or mineral oils, onto the surface of carriers, such as sand, kaolinites or granulated inert material. Suitable active ingredients can also be prepared in the manner customary for the preparation of fertilizer granules—if desired, as a mixture with fertilizers.

In the case of herbicidal agents, the concentrations of the active ingredients in the commercial formulations can vary.

In wettable powders, the active ingredient concentration varies, for example, between about 10% and 80%, and the remainder comprises the formulation additives given above. In the case of emulsifiable concentrates, the active ingredient concentration can also be about 10% to 80%. Formulations in dust form contain about 2–20%. In the case of granules, the active ingredient content depends in part on whether the active compound is present in liquid or solid form, and on which granulation auxiliaries, fillers, etc. are used.

For use as herbicides, the commercial concentrates are diluted in the customary manner, if appropriate, water being used, for example, in the case of wettable powders and emulsifiable concentrates. Granulated preparations and preparations in dust form, and spraying solutions, are not diluted with further inert substances before use. The amount required for use varies with the external conditions, such as temperature, humidity, and the like. It is in general between 0.01 and 10 kg/hectare, preferably about 0.1 to 5.0 kg/hectare of active ingredient.

For some end uses, it can be advantageous to use the new herbicides together with one or more herbicides, for example as a tank mixture or in the form of a ready-prepared formulation, to achieve further advantageous effects.

The active ingredients according to the invention can be combined with other herbicides, insecticides and fungicides.

For use as growth regulators, concentrations between 0.01 and 1.25 kg/hectare are suitable. Aqueous dispersions of wettable powders or dilutions of emulsifiable concentrates are preferably used. The substances are used by the post-emergence method. Preferred crops are maize and tobacco.

PREPARATION EXAMPLES

Example 1

N-(4-Methoxy-6-methyl-1,3,5-triazin-2-yl)-N'-(2,2,2-trichloro-eth-1-oxysulfonyl)-urea 14.0 g (0.1 mole) of 2-amino-4-methoxy-6-methyl-1,3,5-triazine were suspended in 250 ml of dichloromethane, and a solution of 25.5 g (0.1 mole) of 2,2,2-trichloro-eth-1-oxysulfonyl isocyanate in 100 ml of dichloromethane was added dropwise at 0° to 5° C. The reaction mixture was further stirred for 18 hours at room temperature and cooled to 0° C., and n-hexane was added. The precipitated reaction product was filtered off under suction and recrystallized from absolute ethanol. 35.3 g (89.4% of theory) of N-(4-methoxy-6-methyl-1,3,5-triazin-2-yl)-N'-(2,2,2-trichloro-eth-1-oxy-sulfonyl)-urea of melting point 128° C. were obtained.

EXAMPLE 2

N-(4,6-Dimethoxy-1,3,5-triazin-2-yl)-N'-(2-chloro-n-prop-1-yl-sulfonyl)-urea 15.6 g (0.1 mole) of 2-amino-4,6-dimethoxy-1,3,5-triazine were suspended in 150 ml of dichloromethane, and a solution of 19.5 g (0.106 mole) of 2-chloro-n-prop-1-yl-sulfonyl isocyanate in 100 ml of dichloromethane was added at 0° C., while stirring. The mixture was further stirred for 12 hours at room temperature and cooled to 0° C., and 300 ml of n-hexane were added. The precipitated reaction product was filtered off under suction, washed with n-hexane and dried. 30.7 g (90.5% of theory) of N-(4,6-dimethoxy-1,3,5-triazin-2-yl)-N'-(2-chloro-n-prop-1-yl-sulfonyl)-urea of melting point 139°–41° C. were obtained.

EXAMPLE 3

N-(4,6-Dimethyl-5-chloro-pyrimidin-2-yl)-N'-(1,2-dichloro-n-prop-1-yl-sulfonyl)-urea 15.3 g (0.05 mole) of N-(4,6-dimethyl-5-chloro-pyrimidin-2-yl)-N'-(n-prop-1-en-1-yl-sulfonyl)-urea (cf. Example 23) were suspended in 300 ml of dichloromethane and chlorinated for 30 minutes under UV irradiation. The precipitated reaction product was filtered off under suction and washed with n-hexane. After recrystallization from chloroform, 14.6 g (78% of theory) of N-(4,6-dimethyl-5-chloro-pyrimidin-2-yl)-N'-(1,2-dichloro-n-prop-1-yl-sulfonyl)-urea of melting point 161°–2° C. were obtained.

EXAMPLE 4

N-(4,6-Dimethyl-pyrimidin-2-yl)-N'-(vinylsulfonyl)-urea 14.6 g (0.05 mole) of N-(4,6-dimethyl-pyrimidin-2-yl)-N'-(2-chloro-eth-1-yl-sulfonyl)-urea (cf. Example 12) were dissolved in 150 ml of ethanol, and 4 g (0.1 mole) of sodium hydroxide, dissolved in 10 ml of water, were added at room temperature. The reaction mixture was then warmed to 40° C. for 4 hours, concentrated in vacuo and taken up in 150 ml of water. After acidification with 2 N HCl (pH 5), the mixture was extracted with ethyl acetate, and the extracts were then dried and concentrated. After the addition of n-hexane, 8.9 g (69.5% of theory) of N-(4,6-dimethyl-pyrimidin-2-yl)-N'-(vinylsulfonyl)-urea of melting point 131°–3° C. were obtained.

In a similar manner the following compounds can be (or, if accompanied by melting points, have been) prepared:

TABLE 1

$$R_1-(O)_m-SO_2-N(R_2)-\overset{O}{\underset{\|}{C}}-N(R_3)-R_4$$

| Example No. | $R_1$ | m | $R_2$ | $R_3$ | $R_4$ | Melting point [°C.] |
|---|---|---|---|---|---|---|
| 5 | $CCl_3CH_2-$ | 1 | H | H | 4-OCH₃, 6-CH₃ pyrimidin-2-yl | 155–60 |
| 6 | $CF_3CH_2-$ | 1 | H | H | 4-OCH₃, 6-CH₃ pyrazin-2-yl | 128–33 |
| 7 | $CF_3CH_2-$ | 1 | H | H | 4-OCH₃, 6-CH₃ pyrimidin-2-yl | 120–30 |

TABLE 1-continued $$R_1-(O)_m-SO_2-\underset{R_2}{N}-\overset{\overset{O}{\|}}{C}-\underset{R_3}{N}-R_4$$

| Example No. | $R_1$ | m | $R_2$ | $R_3$ | $R_4$ | Melting point [°C.] |
|---|---|---|---|---|---|---|
| 8 | $CH_2Cl-CH(CH_2Cl)-$ | 1 | H | H | 4-methoxy-6-methylpyrimidin-2-yl | 132–6 |
| 9 | $CH_2Cl-CH(CH_2Cl)-$ | 1 | H | H | 4-methoxy-6-methylpyridin-2-yl | 127–133 |
| 10 | $CH_3-CH(CCl_3)-$ | 1 | H | H | 4-methoxy-6-methylpyridin-2-yl | 143–6 |
| 11 | $CH_3-CH(CCl_3)-$ | 1 | H | H | 4,6-dimethylpyridin-2-yl | |
| 12 | $CH_2=CH-CH_2-$ | 1 | H | H | 4,6-dimethoxypyrimidin-2-yl | 80–2 |
| 13 | $CHCl_2-CH(CHCl_2)-$ | 1 | H | H | 4-methoxy-6-methylpyridin-2-yl | |
| 14 | $(CH_3)_2CH-CH_2-$ | 1 | H | H | 4,6-dimethylpyridin-2-yl | 140–3 |
| 15 | $CH_3CH_2-CH(CH_3)-$ | 1 | H | H | 4,6-dimethylpyridin-2-yl | |

TABLE 1-continued $$R_1-(O)_m-SO_2-\underset{R_2}{N}-\underset{\|}{\overset{O}{C}}-\underset{R_3}{N}-R_4$$

| Example No. | $R_1$ | m | $R_2$ | $R_3$ | $R_4$ | Melting point [°C.] |
|---|---|---|---|---|---|---|
| 16 | $CCl_3-\underset{CH_3}{\overset{CH_3}{\underset{|}{C}}}-$ | 1 | H | H | pyrimidine with $OCH_3$ and $CH_3$ | |
| 17 | $\underset{CF_3}{\overset{CF_3}{\diagdown}}CH-$ | 1 | H | H | pyrimidine with $OCH_3$ and $CH_3$ | |
| 18 | $BrCH_2CHBrCH_2-$ | 1 | H | H | pyrimidine with $OCH_3$ and $CH_3$ | |
| 19 | $ClCH_2CH_2-$ | 0 | H | H | pyrimidine with $CH_3$ and $CH_3$ | 95–6 |
| 20 | $ClCH_2CH_2-$ | 0 | H | H | pyrimidine with $OCH_3$ and $CH_3$ | 159–60 |
| 21 | $ClCH_2CH_2-$ | 0 | H | H | pyrimidine with $OCH_3$ and $CH_3$ | 170 |
| 22 | $ClCH_2CH_2-$ | 0 | H | H | pyrimidine with $CH_3$ and $CH_3$ | 165–7 |
| 23 | $Cl_2CHCH_2-$ | 0 | H | H | pyrimidine with $OCH_3$ and $CH_3$ | 142–3 |

TABLE 1-continued $$R_1-(O)_m-SO_2-\underset{R_2}{N}-\underset{\parallel}{\overset{O}{C}}-\underset{R_3}{N}-R_4$$

| Example No. | $R_1$ | m | $R_2$ | $R_3$ | $R_4$ | Melting point [°C.] |
|---|---|---|---|---|---|---|
| 24 | $Cl_2CHCH_2-$ | 0 | H | H | pyrimidine with $OCH_3$, $CH_3$ | 133–5 |
| 25 | $ClCH_2CHCl-$ | 0 | H | H | pyrimidine with $OCH_3$, $CH_3$ | 110–2 |
| 26 | $BrCH_2CHBr-$ | 0 | H | H | pyrimidine with $OCH_3$, $CH_3$ | |
| 27 | $CH_2=CH-$ | 0 | H | H | pyrimidine with $OCH_3$, $CH_3$ | 147–50 |
| 28 | $CH_2=CH-$ | 0 | H | H | pyrimidine | 183–5 |
| 29 | $ClCH=CH-$ | 0 | H | H | pyridine with $OCH_3$, $CH_3$ | |
| 30 | $CH_2=\underset{Br}{C}-$ | 0 | H | H | pyrimidine with $OCH_3$, Cl, $CH_3$ | |
| 31 | $CH_3CHCH_2-$ $\;\;\;\;\;\;\;\;\underset{Cl}{\mid}$ | 0 | H | H | pyrimidine with $OCH_3$, $CH_3$ | 116–8 |

TABLE 1-continued $$R_1-(O)_m-SO_2-\underset{R_2}{N}-\overset{\overset{O}{\|}}{C}-\underset{R_3}{N}-R_4$$

| Example No. | $R_1$ | m | $R_2$ | $R_3$ | $R_4$ | Melting point [°C.] |
|---|---|---|---|---|---|---|
| 32 | $CH_3-\underset{Cl}{CH}CH_2-$ | 0 | H | H | 2,6-dimethylpyrimidin-4-yl (CH₃ at 4 and 6 positions) | 165–7 |
| 33 | $CH_3\underset{Cl}{CH}CH_2-$ | 0 | H | H | 4-OCH₃-6-CH₃-pyrimidin-2-yl | 137–42 |
| 34 | $CH_3\underset{Cl}{CH}CH_2-$ | 0 | H | H | 4,6-dimethoxypyrimidin-2-yl | 165–7 |
| 35 | $CH_3\underset{Cl}{CH}CH_2-$ | 0 | H | H | 4,6-dimethoxy-1,3,5-triazin-2-yl | 139–41 |
| 36 | $CH_3\underset{Cl}{CH}CH_2-$ | 0 | H | H | 4-SCH₃-6-CH₃-1,3,5-triazin-2-yl | 158–60 |
| 37 | $CH_3\underset{Cl}{CH}CH_2-$ | 0 | H | H | 4-OCH₃-6-COOC₂H₅-pyrimidin-2-yl | 89 |
| 38 | $CH_3\underset{Cl}{CH}CH_2-$ | 0 | H | H | 4,6-dimethoxy-5-C₂H₅-pyrimidin-2-yl | 174–6 |
| 39 | $CH_3\underset{Cl}{CH}CH_2-$ | 0 | H | H | 4-C₂F₅-pyrimidin-2-yl | 153–4 |

TABLE 1-continued $$R_1-(O)_m-SO_2-\underset{R_2}{N}-\underset{\parallel}{\overset{O}{C}}-\underset{R_3}{N}-R_4$$

| Example No. | R₁ | m | R₂ | R₃ | R₄ | Melting point [°C] |
|---|---|---|---|---|---|---|
| 40 | CH₃CHCH₂— <br> \|<br>Cl | 0 | H | H | 4-methyl-6-methyl-pyrimidin-2-yl with COOC₂H₅ | 149–52 |
| 41 | CH₃CHCH₂— <br> \|<br>Cl | 0 | H | H | 4,6-dimethyl-5-chloro-pyrimidin-2-yl | 149 |
| 42 | CH₃CH=CH— | 0 | H | H | 4,6-dimethyl-pyrimidin-2-yl | 158–61 |
| 43 | CH₃CH=CH— | 0 | H | H | 4,6-dimethyl-pyrazin-2-yl | 154–8 |
| 44 | CH₃CH=CH— | 0 | H | H | 4-OCH₃-6-CH₃-pyrimidin-2-yl | 215–9 |
| 45 | CH₃CH=CH— | 0 | H | H | 4-OCH₃-6-CH₃-pyrazin-2-yl | 172–3 |
| 46 | CH₃CH=CH— | 0 | H | H | 4,6-di-OCH₃-pyrimidin-2-yl | 202–3 |
| 47 | CH₃CH=CH— | 0 | H | H | 4,6-di-OCH₃-pyrazin-2-yl | 165–8 |

TABLE 1-continued $$R_1-(O)_m-SO_2-\underset{R_2}{N}-\underset{\parallel}{\overset{O}{C}}-\underset{R_3}{N}-R_4$$

| Example No. | $R_1$ | m | $R_2$ | $R_3$ | $R_4$ | Melting point [°C.] |
|---|---|---|---|---|---|---|
| 48 | $CH_3CH=CH-$ | 0 | H | H | pyrimidine with CH₃, SCH₃, CH₃ substituents | 176-8 |
| 49 | $CH_3CH=CH-$ | 0 | H | H | pyrimidine with CH₃, CH₃, Cl, CH₃ substituents | 111 |
| 50 | $CH_3CH=CH-$ | 0 | H | H | pyrimidine with CH₃, $OC_2H_5$, CH₃ substituents | 204-6 |
| 51 | $CH_3CH=CH-$ | 0 | H | H | pyrimidine with CH₃, $OC_3H_7(n)$, CH₃ substituents | 159-61 |
| 52 | $CH_3CH=CH-$ | 0 | H | H | triazine with CH₃, $OCH_3$, $C_2H_5$ substituents | 142-4 |
| 53 | $CH_3CH=CH-$ | 0 | H | H | triazine with CH₃, $OC_2H_5$, CH₃ substituents | 154-7 |
| 54 | $CH_3CH=CH-$ | 0 | H | H | triazine with CH₃, $OCH_3$, $C_3H_7$(iso) substituents | 114-6 |
| 55 | $CH_3\underset{Cl}{C}H\underset{Cl}{C}H-$ (THREO) | 0 | H | H | pyrimidine with CH₃, CH₃, CH₃ substituents | 110-2 |

TABLE 1-continued $$R_1-(O)_m-SO_2-\underset{R_2}{N}-\overset{O}{\underset{}{C}}-\underset{R_3}{N}-R_4$$

| Example No. | R₁ | m | R₂ | R₃ | R₄ | Melting point [°C.] |
|---|---|---|---|---|---|---|
| 56 | CH₃CHCH— (THREO)<br>    \|  \|<br>   Cl  Cl | 0 | H | H | pyrimidine with OCH₃, CH₃ | 166–7 |
| 57 | CH₃CHCH— (THREO)<br>   Cl  Cl | 0 | H | H | pyrimidine with OCH₃, CH₃ | 130 |
| 58 | CH₃CHCH— (THREO)<br>   Cl  Cl | 0 | H | H | pyrimidine with OCH₃, OCH₃ | 170–2 |
| 59 | CH₃CHCH— (THREO)<br>   Cl  Cl | 0 | H | H | pyrimidine with OCH₃, OCH₃ | 139–42 |
| 60 | CH₃CHCH (THREO)<br>   Cl  Cl | 0 | H | CH₃ | pyrimidine with OCH₃, OCH₃ | 101–2 |
| 61 | CH₃CHCH— (THREO)<br>   Cl  Cl | 0 | H | H | pyrimidine with SCH₃, CH₃ | 124–6 |
| 62 | CH₃CHCH— (THREO)<br>   Cl  Cl | 0 | H | H | pyrimidine with N(CH₃)₂, CH₃ | 141–3 |
| 63 | CH₃CHCH— (THREO)<br>   Cl  Cl | 0 | H | H | pyrimidine with OC₂H₅, CH₃ | 98–102 |

TABLE 1-continued $$R_1-(O)_m-SO_2-\underset{R_2}{N}-\underset{\|}{\overset{O}{C}}-\underset{R_3}{N}-R_4$$

| Example No. | $R_1$ | m | $R_2$ | $R_3$ | $R_4$ | Melting point [°C.] |
|---|---|---|---|---|---|---|
| 64 | CH₃CHCH— (THREO)<br>  \|   \|<br>  Cl  Cl | 0 | H | H | pyrimidine with C₃H₇(n) and OCH₃ | Resin |
| 65 | CH₃CHCH— (THREO)<br>  \|   \|<br>  Cl  Cl | 0 | H | H | pyrimidine with C₃H₇(iso) and OCH₃ | Resin |
| 66 | CH₃CHCH— (THREO)<br>  \|   \|<br>  Cl  Cl | 0 | H | H | pyrimidine with OCH₃ and C₂H₅ | 50-3 |
| 67 | CH₃CHCH— (THREO)<br>  \|   \|<br>  Cl  Cl | 0 | H | H | pyrimidine with OC₃H₇(n) and CH₃ | 112-4 |
| 68 | CH₃CHCH— (ERYTHRO)<br>  \|   \|<br>  Cl  Cl | 0 | H | H | pyrimidine with OCH₃ and CH₃ | 124-30 |
| 69 | ClCH₂CHCH₂—<br>         \|<br>         Cl | 0 | H | H | pyrimidine with OCH₃ and CH₃ | 131-4 |
| 70 | ClCH₂CHCH₂—<br>         \|<br>         Cl | 0 | H | H | pyrimidine with OCH₃ and CH₃ | 128-30 |
| 71 | ClCH₂CHCH₂—<br>         \|<br>         Cl | 0 | H | H | pyrimidine with OCH₃ and OCH₃ | 111-3 |

TABLE 1-continued $$R_1-(O)_m-SO_2-\underset{R_2}{N}-\overset{O}{\underset{\|}{C}}-\underset{R_3}{N}-R_4$$

| Example No. | $R_1$ | m | $R_2$ | $R_3$ | $R_4$ | Melting point [°C.] |
|---|---|---|---|---|---|---|
| 72 | BrCH$_2$CHClCH$_2$— | 0 | H | H | pyrimidinyl (OCH$_3$, CH$_3$) | |
| 73 | ClCH$_2$-CH=CH— | 0 | H | H | pyrimidinyl (OCH$_3$, CH$_3$) | 163–7 |
| 74 | CH$_3$-C(H)=C(Cl)— | 0 | H | H | pyrimidinyl (OCH$_3$, CH$_3$) | 151–3 |
| 75 | CH$_3$-C(H)=C(Cl)— | 0 | H | H | pyrimidinyl (OCH$_3$, CH$_3$) | 95 |
| 76 | CH$_3$-C(H)=C(Cl)— | 0 | H | H | pyrimidinyl (OCH$_3$, CH$_3$) | 164–7 |
| 77 | CH$_3$CHClCH(CH$_3$)— | 0 | H | H | pyrimidinyl (CH$_3$, CH$_3$) | 112–4 |
| 78 | CH$_3$CHClCH(CH$_3$)— | 0 | H | H | pyrimidinyl (OCH$_3$, CH$_3$) | 139–40 |
| 79 | CH$_3$CHClCH(CH$_3$)— | 0 | H | H | pyrimidinyl (OCH$_3$, CH$_3$) | 136–8 |

TABLE 1-continued $$R_1-(O)_m-SO_2-N(R_2)-\overset{O}{\underset{}{C}}-N(R_3)-R_4$$

| Example No. | $R_1$ | m | $R_2$ | $R_3$ | $R_4$ | Melting point [°C.] |
|---|---|---|---|---|---|---|
| 80 | CH₃CHCH— \| \| Cl CH₃ | 0 | H | H | 2,6-dimethyl-4-(SCH₃)-pyrazinyl | 158–60 |
| 81 | CH₃CHCH— \| \| Cl CH₃ | 0 | H | H | 2,6-dimethyl-4-N(C₂H₅)₂-pyrazinyl | 108–10 |
| 82 | CH₃CHCH— \| \| Cl CH₃ | 0 | H | H | 2,6-dimethyl-4-OC₂H₅-pyrazinyl | 99–102 |
| 83 | CH₃CHCH— \| \| Cl CH₃ | 0 | H | H | 2,6-dimethyl-4-SCH₃-pyrimidinyl | 116–20 |
| 84 | CH₃CHCH— \| \| Cl CH₃ | 0 | H | H | 2-methyl-6-ethyl-4-OCH₃-pyrazinyl | 121–3 |
| 85 | CH₃CHCH— \| \| Cl CH₃ | 0 | H | H | 2,6-dimethyl-4-OC₂H₅-pyrimidinyl | 116–8 |
| 86 | CH₃CH₂CHCH₂— \| Cl | 0 | H | H | 2,4,6-trimethyl-pyrimidinyl | 120–1 |
| 87 | CH₃CH₂CHCH₂— \| Cl | 0 | H | H | 2,6-dimethyl-4-OCH₃-pyrazinyl | Resin |

TABLE 1-continued $$R_1-(O)_m-SO_2-\underset{R_2}{N}-\overset{O}{\underset{}{C}}-\underset{R_3}{N}-R_4$$

| Example No. | $R_1$ | m | $R_2$ | $R_3$ | $R_4$ | Melting point [°C.] |
|---|---|---|---|---|---|---|
| 88 | $CH_3-\underset{\underset{Cl}{|}}{\overset{\overset{CH_3}{|}}{C}}-CH_2-$ | 0 | H | H | pyrimidine with OCH$_3$, CH$_3$, CH$_3$ | Resin |
| 89 | $CH_3-\underset{\underset{Cl}{|}}{\overset{\overset{CH_3}{|}}{C}}-CH_2-$ | 0 | H | H | pyrimidine with CH$_3$, CH$_3$, CH$_3$ | Resin |
| 90 | $CH_3CHCHCH_2-$ with Cl, Cl | 0 | H | H | pyrimidine with CH$_3$, CH$_3$, CH$_3$ | Resin |
| 91 | $CH_3CHCHCH_2-$ with Cl, Cl | 0 | H | H | pyrimidine with OCH$_3$, CH$_3$, CH$_3$ | Resin |
| 92 | $ClCH_2-\underset{\underset{Cl}{|}}{\overset{\overset{CH_3}{|}}{C}}-CH_2-$ | 0 | H | H | pyrimidine with CH$_3$, CH$_3$, CH$_3$ | 164–6 |
| 93 | $ClCH_2-\underset{\underset{Cl}{|}}{\overset{\overset{CH_3}{|}}{C}}CH_2-$ | 0 | H | H | pyrimidine with OCH$_3$, CH$_3$, CH$_3$ | 131–4 |
| 94 | $CHCl_2CH_2CHCH_2-$ with Cl | 0 | H | H | pyrimidine with OCH$_3$, CH$_3$, CH$_3$ | 105 |
| 95 | $CHCl_2CH_2CHCH_2-$ with Cl | 0 | H | H | pyrimidine with OCH$_3$, CH$_3$, CH$_3$ | 120 |

TABLE 1-continued $$R_1-(O)_m-SO_2-N(R_2)-\underset{\underset{}{\overset{O}{\|}}}{C}-N(R_3)-R_4$$

| Example No. | R₁ | m | R₂ | R₃ | R₄ | Melting point [°C.] |
|---|---|---|---|---|---|---|
| 96 | CHCl₂CH₂CHCH— <br>            \|  \| <br>           Br Br | 0 | H | H | 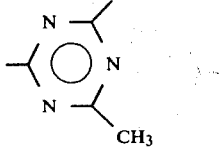 (OCH₃, CH₃ pyrimidine) | Resin |
| 97 | CHCl₂CH₂CHCH— <br>            \|  \| <br>           Br Br | 0 | H | H | 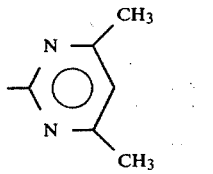 (CH₃, CH₃ pyrimidine) | 85–90 |
| 98 | CH₃CHCH— <br>     \|   \| <br>    Cl CH₂Cl | 0 | H | H | 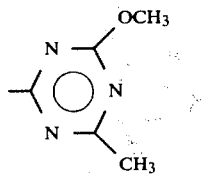 (OCH₃, CH₃ pyrimidine) | Resin |
| 99 | CH₃CHCH— <br>     \|   \| <br>    Cl CH₂Cl | 0 | H | H | (CH₃, CH₃ pyrimidine) | Resin |
| 100 | CHClBrCHBrCHBrCHBr | 0 | H | H | (CH₃, CH₃ pyrimidine) | 140–4 |
| 101 | CHClBrCHBrCHBrCHBr | 0 | H | H | 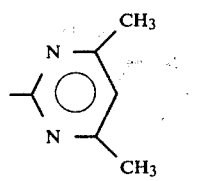 (OCH₃, CH₃ pyrimidine) | |
| 102 | CH₃OCH₂CHCH₂— <br>           \| <br>          Cl | 0 | H | H | 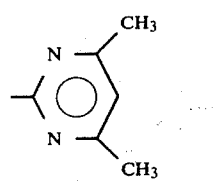 (OCH₃, CH₃ pyrimidine) | 144–6 |
| 103 | CH₃OCH₂CHCH₂— <br>           \| <br>          Cl | 0 | H | H | 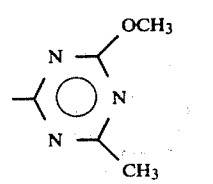 (OCH₃, CH₃ pyrimidine) | 117–20 |

TABLE 1-continued $$R_1-(O)_m-SO_2-\underset{R_2}{N}-\underset{}{\overset{\overset{O}{\|}}{C}}-\underset{R_3}{N}-R_4$$

| Example No. | $R_1$ | m | $R_2$ | $R_3$ | $R_4$ | Melting point [°C] |
|---|---|---|---|---|---|---|
| 104 | $CH_3CH_2CH=CH-$ | 0 | H | H | 4,6-dimethyl-pyrimidin-2-yl (CH$_3$, CH$_3$) | 143-6 |
| 105 | $CH_3CH_2CH=CH-$ | 0 | H | H | 4-methoxy-6-methyl-pyrimidin-2-yl (OCH$_3$, CH$_3$) | 136-9 |
| 106 | $CH_3CH=C(CH_3)-$ | 0 | H | H | 4,6-dimethyl-pyrimidin-2-yl (CH$_3$, CH$_3$) | 167-71 |
| 107 | $CH_3CH=C(CH_3)-$ | 0 | H | H | 4-methoxy-6-methyl-pyrimidin-2-yl (OCH$_3$, CH$_3$) | 148-54 |
| 108 | $CH_3CH=C(CH_3)-$ | 0 | H | H | 4,6-dimethoxy-pyrimidin-2-yl (OCH$_3$, OCH$_3$) | 143-6 |
| 109 | $CH_3CH=C(CH_3)-$ | 0 | H | H | 4,6-dimethoxy-1,3,5-triazin-2-yl (OCH$_3$, OCH$_3$) | 158 |
| 110 | $CH_3CH=C(CH_3)-$ | 0 | H | H | 4,6-dimethoxy-1,3,5-triazin-2-yl (OCH$_3$, OCH$_3$) | 121-123 |
| 111 | $CH_3CH=C(CH_3)-$ | 0 | H | H | 4-methylthio-6-methyl-pyrimidin-2-yl (SCH$_3$, CH$_3$) | 153-6 |

TABLE 1-continued $$R_1-(O)_m-SO_2-N(R_2)-\overset{O}{\underset{}{C}}-N(R_3)-R_4$$

| Example No. | R$_1$ | m | R$_2$ | R$_3$ | R$_4$ | Melting point [°C.] |
|---|---|---|---|---|---|---|
| 112 | CH$_3$CH=C(CH$_3$)— | 0 | H | H | 2-SCH$_3$, 6-CH$_3$-pyrimidin-4-yl | 156–8 |
| 113 | (CH$_3$)(H)C=C(CH$_3$)— | 0 | H | H | 2,6-di-CH$_3$-pyrimidin-4-yl (4-CH$_3$) | 174–6 |
| 114 | (CH$_3$)(H)C=C(CH$_3$)— | 0 | H | H | 2,6-di-CH$_3$-pyrimidin-4-yl | 170–2 |
| 115 | (CH$_3$)(H)C=C(CH$_3$)— | 0 | H | H | 2-OCH$_3$, 6-CH$_3$-pyrimidin-4-yl | 148–9 |
| 116 | (CH$_3$)(H)C=C(CH$_3$)— | 0 | H | H | 2-OCH$_3$, 6-CH$_3$-pyrimidin-4-yl | 151–2 |
| 117 | (CH$_3$)(H)C=C(CH$_3$)— | 0 | H | H | 2-OC$_2$H$_5$, 6-CH$_3$-pyrimidin-4-yl | 128–31 |
| 118 | (CH$_3$)(H)C=C(CH$_3$)— | 0 | H | H | 2-OC$_2$H$_5$, 6-CH$_3$-pyrimidin-4-yl | 157–60 |
| 119 | (CH$_3$)(H)C=C(CH$_3$)— | 0 | H | H | 2-OCH$_3$, 6-C$_2$H$_5$-pyrimidin-4-yl | 130–2 |

TABLE 1-continued $$R_1-(O)_m-SO_2-\underset{R_2}{N}-\underset{}{\overset{\overset{O}{\|}}{C}}-\underset{R_3}{N}-R_4$$

| Example No. | $R_1$ | m | $R_2$ | $R_3$ | $R_4$ | Melting point [°C.] |
|---|---|---|---|---|---|---|
| 120 | $\underset{H}{\overset{CH_3}{C}}=\underset{}{\overset{CH_3}{C}}$ | 0 | H | H | 4-OCH$_3$, 6-C$_2$H$_5$ pyrimidin-2-yl | 140–2 |
| 121 | CHCl$_2$CH$_2$—CH=CH— | 0 | H | H | 4-OCH$_3$, 6-CH$_3$ pyrimidin-2-yl | Resin |
| 122 | CHCl$_2$CH$_2$CH=CH— | 0 | H | H | 4-CH$_3$, 6-CH$_3$ pyrimidin-2-yl | Resin |
| 123 | CH$_3$CHClCH=CH— | 0 | H | H | 4-CH$_3$, 6-CH$_3$ pyrimidin-2-yl | 169–173 |
| 124 | $\underset{ClCH_2}{\overset{CH_3}{C}}=\underset{}{\overset{H}{C}}$ | 0 | H | H | 4-CH$_3$, 6-CH$_3$ pyrimidin-2-yl | Resin |
| 125 | CH$_3$CHC(Cl)(Cl)CH$_3$ | 0 | H | H | 4-CH$_3$, 6-CH$_3$ pyrimidin-2-yl | |
| 126 | CH$_3$CHC(Cl)(Cl)CH$_3$ | 0 | H | H | 4-OCH$_3$, 6-CH$_3$ pyrimidin-2-yl | |
| 127 | CH$_3$CHC(Cl)(Cl)CH$_3$ | 0 | H | H | 4-OCH$_3$, 6-CH(CH$_3$) pyrimidin-2-yl | Resin |

TABLE 1-continued $$R_1-(O)_m-SO_2-\underset{R_2}{N}-\overset{O}{\underset{}{C}}-\underset{R_3}{N}-R_4$$

| Example No. | $R_1$ | m | $R_2$ | $R_3$ | $R_4$ | Melting point [°C.] |
|---|---|---|---|---|---|---|
| 128 | CH₃CHC(Br)(Br)C(CH₃)- | 0 | H | H | 4-OCH₃-6-CH₃-pyrimidin-2-yl | 142-4 |
| 129 | CH₃CHC(Br)(Br)C(CH₃)- | 0 | H | H | 4-OCH₃-6-CH₃-pyrimidin-2-yl (isomer) | 58-60 |
| 130 | (CH₃)(Cl)C=C(CH₃)- | 0 | H | H | 4-OCH₃-6-CH₃-pyrimidin-2-yl | Resin |
| 131 | (CH₃)(Cl)C=C(CH₃)- | 0 | H | H | 4-OCH₃-6-CH₃-pyrimidin-2-yl | |
| 132 | (CH₃)(Br)C=C(CH₃)- | 0 | H | H | 4-OCH₃-6-CH₃-pyrimidin-2-yl | |
| 133 | (CH₃)(Br)C=C(CH₃)- | 0 | H | H | 4-OCH₃-6-CH₃-pyrimidin-2-yl | |
| 134 | ClCH=CH—CH=CH— | 0 | H | H | 4,6-(CH₃)₂-pyrimidin-2-yl | 130-3 |
| 135 | Cl₂CH—CH=CH— | 0 | H | CH₃ | 4-OCH₃-6-CH₃-pyrimidin-2-yl | 144-8 |

TABLE 1-continued $$R_1-(O)_m-SO_2-\underset{R_2}{N}-\underset{\parallel}{\overset{O}{C}}-\underset{R_3}{N}-R_4$$

| Example No. | $R_1$ | m | $R_2$ | $R_3$ | $R_4$ | Melting point [°C.] |
|---|---|---|---|---|---|---|
| 136 | CH$_3$(CH$_2$)CHCH$_2$—<br>\|<br>Cl | 0 | H | H | 4-OCH$_3$, 6-CH$_3$-pyrimidin-2-yl | Resin |
| 137 | CH$_3$(CH$_2$)$_2$CHCH$_2$—<br>\|<br>Cl | 0 | H | H | 4-OCH$_3$, 6-CH$_3$-pyrimidin-2-yl | 167 |
| 138 | CH$_3$CH$_2$CHCH—<br>\|  \|<br>Cl CH$_3$ | 0 | H | H | 4-OCH$_3$, 6-CH$_3$-pyrimidin-2-yl | 124–7 |
| 139 | CH$_3$CH$_2$CHCH—<br>\|  \|<br>Cl CH$_3$ | 0 | H | H | 4,6-di-CH$_3$-pyrimidin-2-yl | Resin |
| 140 | CH$_3$(CH$_2$)$_2$CH=CH— | 0 | H | H | 4-OCH$_3$, 6-CH$_3$-pyrimidin-2-yl | |
| 141 | CH$_3$(CH$_2$)$_2$CH=CH— | 0 | H | H | 4,6-di-CH$_3$-pyrimidin-2-yl | |
| 142 | CH$_3$(CH$_2$)$_2$CH=CH— | 0 | H | H | 4-OC$_2$H$_5$, 6-CH$_3$-pyrimidin-2-yl | |
| 143 | CH$_3$(CH$_2$)$_2$CH=CH— | 0 | H | H | 4-OCH$_3$, 6-CH$_3$-pyrimidin-2-yl | 180–3 |

TABLE 1-continued $$R_1-(O)_m-SO_2-\underset{R_2}{N}-\overset{\overset{O}{\|}}{C}-\underset{R_3}{N}-R_4$$

| Example No. | $R_1$ | m | $R_2$ | $R_3$ | $R_4$ | Melting point [°C.] |
|---|---|---|---|---|---|---|
| 144 | $(CH_3)_2C=C(CH_3)_2$ | 0 | H | H | pyrimidine with $OCH_3$, $CH_3$, $CH_3$ | Resin |
| 145 | $CH_3(CH_2)_3CHClCH_2-$ | 0 | H | H | pyrimidine with $OCH_3$, $CH_3$, $CH_3$ | Oil |
| 146 | $CH_3(CH_2)_3CHClCH_2-$ | 0 | H | H | pyridine with $CH_3$, $CH_3$, $CH_3$ | |
| 147 | $CH_3(CH_2)_3CHClCH_2-$ | 0 | H | H | pyridine with $CH_3$, $CH_3$, $OC_2H_5$, $CH_3$ | 72-3 |
| 148 | $CH_3(CH_2)_3CH=CH-$ | 0 | H | H | pyridine with $CH_3$, $CH_3$, $CH_3$ | 142-3 |
| 149 | $CH_3(CH_2)_3CH=CH-$ | 0 | H | H | pyridine with $OCH_3$, $CH_3$, $CH_3$ | 153-7 |
| 150 | $CH_3(CH_2)_3CH=CH-$ | 0 | H | H | pyrimidine with $OCH_3$, $CH_3$ | 144 |
| 151 | $CH_3(CH_2)_3CH=CH-$ | 0 | H | H | pyrimidine with $OCH_3$, $C_2H_5$ | 116-9 |

TABLE 1-continued $$R_1-(O)_m-SO_2-N(R_2)-\underset{\underset{}{\overset{O}{\|}}}{C}-N(R_3)-R_4$$

| Example No. | $R_1$ | m | $R_2$ | $R_3$ | $R_4$ | Melting point [°C] |
|---|---|---|---|---|---|---|
| 152 | $CH_3(CH_2)_4CHCH_2-$ with Cl on CH | 0 | H | H | 4,6-dimethylpyrimidin-2-yl | |
| 153 | $CH_3(CH_2)_4CHCH_2-$ with Cl on CH | 0 | H | H | 4-methoxy-6-methylpyrimidin-2-yl | |
| 154 | $CH_3(CH_2)_4CH=CH-$ | 0 | H | H | 4,6-dimethylpyrimidin-2-yl | 125–6 |
| 155 | $CH_3(CH_2)_5CHCH_2-$ with Cl on CH | 0 | H | H | 4,6-dimethylpyrimidin-2-yl | 69–70 |
| 156 | $CH_3(CH_2)_5CHCH_2-$ with Cl on CH | 0 | H | H | 4-methoxy-6-methylpyrimidin-2-yl | |
| 157 | $CH_3(CH_2)_5CH=CH-$ | 0 | H | H | 4,6-dimethylpyrimidin-2-yl | Resin |
| 158 | $CH_3(CH_2)_5CH=CH-$ | 0 | H | H | 4-methoxy-6-methylpyrimidin-2-yl | Resin |
| 159 | $CH_3(CH_2)_6CHCH_2-$ with Cl on CH | 0 | H | H | 4,6-dimethylpyrimidin-2-yl | |

TABLE 1-continued $$R_1-(O)_m-SO_2-\underset{R_2}{N}-\underset{\|}{\overset{O}{C}}-\underset{R_3}{N}-R_4$$

| Example No. | R₁ | m | R₂ | R₃ | R₄ | Melting point [°C.] |
|---|---|---|---|---|---|---|
| 160 | $CH_3(CH_2)_6CH=CH-$ | 0 | H | H | 4,6-dimethylpyrimidin-2-yl | |
| 161 | $CH_3(CH_2)_6CH=CH-$ | 0 | H | H | 4-methoxy-6-methyl-1,3,5-triazin-2-yl | |
| 162 | $CHF_2CF_2OCHClCH_2-$ | 0 | H | H | 4,6-dimethylpyrimidin-2-yl | 48–51 |
| 163 | $CHF_2CF_2OCHClCH_2-$ | 0 | H | H | 4-methoxy-6-methyl-1,3,5-triazin-2-yl | 95–8 |
| 164 | $CH_3-CHCl-CHCl-$ | 0 | H | $CH_3$ | 4,6-dimethyl-1,3,5-triazin-2-yl | 121–3 |

+ E/Z mixture

FORMULATION EXAMPLES

Example A

An emulsifiable concentrate is obtained from: 15 parts by weight of active ingredient, 75 parts by weight of cyclohexane as the solvent and 10 parts by weight of oxyethylated nonylphenol (10 units of ethylene oxide) as the emulsifier.

Example B

A wettable powder which is readily dispersible in water is obtained by mixing 25 parts by weight of active ingredient, 64 parts by weight of kaolin-containing quartz as the inert material, 10 parts by weight of potassium ligninsulfonate and 1 part by weight of sodium oleylmethyltaurate as the wetting agent and dispersing agent, and grinding the mixture in a pinned disk mill.

Example C

A dusting agent is obtained by mixing 10 parts by weight of active ingredient and 90 parts by weight of talc as the inert material, and comminuting the mixture in a beater mill.

Example D

Granules are composed, for example, of about 2–15 parts by weight of active ingredient and 98–85 parts by weight of inert granule material, such as, for example, attapulgite, pumice and quartz sand.

BIOLOGICAL EXAMPLES

(a) Herbicidal action

1. Pre-emergence method

Seed or pieces of rhizome of monocotyledonous and dicotyledonous weeds were placed in loamy soil in plastic pots (ϕ8 cm) and covered with soil. The compounds according to the invention, which were formulated as wettable powders, were applied, in the form of aqueous suspensions or emulsions, onto the soil surface. The amount of water used per pot corresponded to 600–800 l/hectare. After treatment, the experimental pots were placed in a greenhouse and the experimental plants were cultivated under good conditions of growth (temperature: 23°±1° C.; relative atmospheric humidity 60-80%). After about 3 weeks, the damage to the plants was assessed optically. Untreated controls served for comparison.

The damage to the weeds and the tolerance of the cultivated plants were expressed on a scale of 0-5.

The figures denote:
0 = without action (damage)
1 = 0-20% action
2 = 20-40% action
3 = 40-60% action
4 = 60-80% action
5 = 80-100% action The abbreviations denote:
LOM = rye grass
ECG = prickly grass
STM = starwort
AMR = amaranth
SIA = wild mustard
CYE = wood sorrel (perennial)
a.i. = active ingredient The pre-emergence results are summarized in Table 2. It is clear that the compounds according to the invention have a good herbicidal action against monocotyledonous weeds as well as against dicotyledonous weeds when the active ingredients are applied by the pre-emergence method.

TABLE 2

Pre-emergence action against monocotyledonous and dicotyledonous weeds. Effect in % in comparison with the untreated control.

| Example No. | Dose (kg of a.i. per hectare) | SIA | ECG | STM | LOM | AMR | CYE |
|---|---|---|---|---|---|---|---|
| 1 | 2.5 | 4 | 1 | 4 | 0 | 5 | 4 |
|  | 10.0 | — | — | 5 | 1 | — | — |
| 5 | 2.5 | 4 | 1 | 5 | 1 | 3 | 5 |
|  | 10.0 | — | — | 5 | 3 | — | — |
| 6 | 2.5 | 2 | 2 | 4 | 0 | 2 | 4 |
| 7 | 2.5 | 5 | 2 | 5 | 0 | 2 | 5 |
| 19 | 2.5 | 2 | 4 | 4 | 3 | 5 | — |
| 20 | 2.5 | 4 | 3 | 4 | 4 | 2 | 5 |
|  | 10.0 | — | — | 4 | 5 | — | — |
| 23 | 2.5 | 4 | 0 | 5 | 4 | — | — |
| 24 | 2.5 | 4 | 4 | 5 | 5 | — | — |
| 31 | 2.5 | 5 | 5 | 5 | 5 | 5 | 5 |
| 44 | 2.5 | 5 | 5 | 5 | 5 | — | — |
| 45 | 2.5 | 5 | 5 | 5 | 5 | — | — |
| 46 | 2.5 | 4 | 5 | 5 | 5 | — | — |
| 47 | 2.5 | 4 | 3 | 5 | 5 | — | — |
| 48 | 2.5 | 5 | 2 | 4 | 4 | — | — |
| 50 | 2.5 | 5 | 3 | 5 | 5 | — | — |
| 52 | 2.5 | 5 | 4 | 5 | 5 | — | — |
| 53 | 2.5 | 5 | 5 | 5 | 5 | — | — |
| 54 | 2.5 | 3 | 2 | 4 | 3 | — | — |
| 55 | 2.5 | 5 | 5 | 5 | 5 | — | — |
| 56 | 2.5 | 5 | 5 | 5 | 5 | 5 | 5 |
| 57 | 2.5 | 5 | 5 | 5 | 5 | 5 | 5 |
| 64 | 2.5 | 2 | 2 | 5 | 2 | — | — |
| 66 | 2.5 | 5 | 5 | 5 | 5 | — | — |
| 67 | 2.5 | 5 | 3 | 5 | 2 | — | — |
| 69 | 2.5 | 4 | 2 | 5 | 3 | — | — |
| 70 | 2.5 | 5 | 5 | 5 | 5 | — | — |
| 71 | 2.5 | 5 | 5 | 4 | 0 | — | — |
| 74 | 2.5 | 5 | 5 | 5 | 5 | — | — |
| 75 | 2.5 | 5 | 5 | 5 | 5 | — | — |
| 76 | 2.5 | 5 | 5 | 5 | 5 | — | — |
| 78 | 2.5 | 5 | 5 | 5 | 5 | 5 | 5 |
| 79 | 2.5 | 5 | 5 | 5 | 4 | 4 | 5 |
| 83 | 2.5 | 5 | 3 | 5 | 5 | — | — |
| 84 | 2.5 | 5 | 1 | 5 | 3 | — | — |
| 85 | 2.5 | 5 | 4 | 5 | 4 | — | — |
| 98 | 2.5 | 5 | 5 | 5 | 5 | — | — |
| 99 | 2.5 | 5 | 5 | 5 | 5 | — | — |
| 104 | 2.5 | 2 | 0 | 2 | 0 | — | — |
| 106 | 2.5 | 5 | 5 | 5 | 5 | — | — |
| 107 | 2.5 | 5 | 5 | 5 | 5 | — | — |
| 115 | 2.5 | 5 | 5 | 5 | 5 | — | — |
| 116 | 2.5 | 5 | 5 | 5 | 5 | — | — |
| 118 | 2.5 | 5 | 5 | 5 | 5 | — | — |
| 120 | 2.5 | 5 | 5 | 5 | 5 | — | — |
| 123 | 2.5 | 4 | 2 | 3 | 2 | — | — |
| 136 | 2.5 | 5 | 5 | 5 | 5 | — | — |
| 138 | 2.5 | 5 | 5 | 5 | 5 | — | — |
| 139 | 2.5 | 2 | 3 | 4 | 4 | — | — |
| 141 | 2.5 | 5 | 0 | 4 | 3 | — | — |
| 143 | 2.5 | 5 | 5 | 5 | 5 | — | — |
| 148 | 2.5 | 5 | 3 | 5 | 5 | — | — |
| 149 | 2.5 | 5 | 3 | 5 | 4 | — | — |
| 150 | 2.5 | 5 | 4 | 5 | 5 | — | — |

2. Post-emergence method

Seed or pieces of rhizome of monocotyledonous and dicotyledonous weeds were sown in pots and cultivated in a greenhouse under good conditions of growth. 3 weeks after sowing, the experimental plants were treated at the stage when three leaves had developed.

The preparations according to the invention, which were formulated as wettable powders or as emulsion concentrates, were sprayed, in various dosages, onto the green parts of the plants, and after the plants had been standing for about 3 weeks in the greenhouse, the action of the preparations was assessed optically in comparison with untreated controls.

The agents according to the invention have a good herbicidal activity against a broad spectrum of commercially important annual and perennial weeds and graminaceous weeds (Table 3).

TABLE 3

Post-emergence action against monocotyledonous and dicotyledonous weeds. Effect in % in comparison to the untreated control.

| Example No. | Dose (kg of a.i./hectare) | SIA | ECG | STM | LOM | AMR | CYE |
|---|---|---|---|---|---|---|---|
| 1 | 2.5 | 5 | 1 | 4 | 1 | 0 | — |
| 5 | 2.5 | 5 | 1 | 4 | 1 | 0 | — |
| 6 | 2.5 | 4 | 1 | 3 | 1 | 2 | — |
| 7 | 2.5 | 1 | 1 | 3 | 1 | 2 | — |
| 19 | 2.5 | 2 | 1 | 3 | 1 | 3 | — |
| 20 | 2.5 | 5 | 1 | 4 | 2 | 1 | — |
| 23 | 2.5 | 3 | 0 | 3 | 0 | — | — |
| 24 | 2.5 | 3 | 2 | 4 | 3 | — | — |
| 31 | 2.5 | 5 | 4 | 5 | 5 | 5 | — |
| 44 | 2.5 | 5 | 5 | 5 | 5 | — | — |
| 45 | 2.5 | 5 | 5 | 5 | 5 | — | — |
| 46 | 2.5 | 4 | 0 | 4 | 3 | — | — |
| 47 | 2.5 | 5 | 4 | 4 | 3 | — | — |
| 48 | 2.5 | 5 | 0 | 4 | 3 | — | — |
| 50 | 2.5 | 3 | 0 | 3 | 2 | — | — |
| 52 | 2.5 | 5 | 0 | 5 | 5 | — | — |
| 53 | 2.5 | 5 | 3 | 5 | 4 | — | — |
| 54 | 2.5 | 3 | 2 | 2 | 3 | — | — |
| 55 | 2.5 | 4 | 5 | 4 | 4 | — | — |
| 56 | 2.5 | 5 | 4 | 5 | 4 | 5 | 0 |
| 57 | 2.5 | 5 | 3 | 5 | 4 | 5 | 0 |
| 64 | 2.5 | 4 | 2 | 4 | 0 | — | — |
| 66 | 2.5 | 5 | 3 | 5 | 4 | — | — |
| 67 | 2.5 | 3 | — | 2 | 2 | — | — |
| 69 | 2.5 | 5 | — | 4 | 2 | — | — |

TABLE 3-continued

Post-emergence action against monocotyledonous and dicotyledonous weeds. Effect in % in comparison to the untreated control.

| Example No. | Dose (kg of a.i./hectare) | SIA | ECG | STM | LOM | AMR | CYE |
|---|---|---|---|---|---|---|---|
| 70 | 2.5 | 4 | 2 | 4 | 2 | — | — |
| 71 | 2.5 | 4 | 2 | 4 | 2 | — | — |
| 74 | 2.5 | 5 | 5 | 5 | 5 | — | — |
| 75 | 2.5 | 5 | 5 | 5 | 5 | — | — |
| 76 | 2.5 | 5 | 5 | 5 | 5 | — | — |
| 78 | 2.5 | 5 | 4 | 5 | 4 | 5 | — |
| 79 | 2.5 | 5 | 5 | 5 | 4 | 5 | — |
| 83 | 2.5 | 4 | 2 | 3 | 2 | — | — |
| 84 | 2.5 | 5 | 1 | 5 | 0 | — | — |
| 85 | 2.5 | 5 | 2 | 4 | 3 | — | — |
| 98 | 2.5 | 4 | 4 | 3 | 3 | — | — |
| 99 | 2.5 | 4 | 5 | 5 | 4 | — | — |
| 104 | 2.5 | 4 | 2 | 2 | 1 | — | — |
| 105 | 2.5 | 5 | 3 | 4 | 3 | — | — |
| 106 | 2.5 | 5 | 5 | 5 | 5 | — | — |
| 107 | 2.5 | 5 | 5 | 5 | 5 | — | — |
| 115 | 2.5 | 5 | 5 | 5 | 5 | — | — |
| 116 | 2.5 | 5 | 4 | 5 | 5 | — | — |
| 118 | 2.5 | 5 | 5 | 5 | 5 | — | — |
| 120 | 2.5 | 5 | 5 | 5 | 5 | — | — |
| 123 | 2.5 | 2 | 2 | 4 | 3 | — | — |
| 136 | 2.5 | 5 | 3 | 4 | 3 | — | — |
| 138 | 2.5 | 5 | 5 | 5 | 5 | — | — |
| 139 | 2.5 | 5 | 5 | 4 | 3 | — | — |
| 141 | 2.5 | 5 | 3 | 3 | 2 | — | — |
| 143 | 2.5 | 5 | 4 | 4 | 5 | — | — |
| 148 | 2.5 | 5 | 1 | 2 | 3 | — | — |
| 149 | 2.5 | 5 | 3 | 3 | 3 | — | — |
| 150 | 2.5 | 5 | 2 | 4 | 3 | — | — |

(b) Plant growth-regulating action

Example I (Inhibition of growth of cereals)

In experiments in trays in a greenhouse, young cereal plants (wheat, barley and rye), at the stage when they had developed 3 leaves, were sprayed until dripping wet with the given active ingredient concentrations (kg/hectare) of the compound mentioned in Table 1. 2-Chloroethyltrimethylammonium chloride was employed as a comparative compound. After the untreated control plants had reached a height of growth of about 55 cm, the additional growth of all the plants was measured and the inhibition of growth in % of the additional growth of the control plants was calculated. In addition, the phytotoxic action of the compounds was observed. The results are summarized in Table 4. In the case of the growth inhibition data, 100% means that growth has stopped and 0% denotes a growth corresponding to that of the untreated control plants.

TABLE 4

| Compound of Example | Concentration used (kg/hectare) | Inhibition of growth in % | | | Phytotoxic action |
|---|---|---|---|---|---|
| | | Wheat | Barley | Rye | |
| 56 | 0.62 | 34 | 32 | 27 | no |
| | 0.31 | 32 | 28 | 25 | damage |
| 31 | 0.62 | 34 | 27 | 24 | no |
| | 0.31 | 23 | 24 | 19 | damage |
| Comparison (2-Chloroethyl)-trimethylammonium chloride | 2.5 | 28 | 8 | 9 | no |
| | 1.25 | 20 | 0 | 0 | damage |

Example II (Inhibition of growth of soybean and bush bean)

10–15 cm high soybeans or bush beans were sprayed with the preparations of active ingredient until dripping wet. After 2 weeks, the additional growth was measured and the inhibition of growth in % of the additional growth of the control plants was calculated. The results are summarized in Table 5.

TABLE 5

Inhibition of growth of soybean and bush bean

| Compound of Example | Concentration used (kg/hectare) | Inhibition of growth in % | | Phytotoxic action |
|---|---|---|---|---|
| | | Soybean | Bush bean | |
| 56 | 0.62 | 23 | 42 | no |
| | 0.31 | 21 | 39 | damage |
| 31 | 0.62 | 24 | 37 | no damage |
| $\begin{array}{l}CH_2-CO-NH-N<_{CH_3}^{CH_3}\\ |\\ CH_2-COOH\end{array}$ (Aminozide) | 2.5 | 12 | 34 | no damage |

Example III (Inhibition of growth of lawns)

A lawn mixture, comprising 5 representative species, was sprayed with a preparation of active ingredient until dripping wet, after having been cut back 3 times. After 3–4 weeks, the additional growth was measured and the inhibition of growth in % of the additional growth of the control plants was calculated. 100% means that growth has stopped and 0% denotes a growth corresponding to that of the untreated control plants.

TABLE 6

Inhibition of growth of lawns

| Compound of Example | Concentration used (kg/hectare) | Inhibition of growth in % | Phytotoxic action |
|---|---|---|---|
| 56 | 0.62 | 54 | no |
| | 0.31 | 37 | damage |
| 31 | 0.62 | 45 | no |
| | 0.31 | 42 | damage |
| maleic acid hydrazide | 2.5 | 55 | severe damage |

Example IV (Increase in the sugar content of sugar cane

Method of investigation

Sugar cane plants were cultivated under greenhouse conditions at 25° C.–35° C. and an atmospheric humidity of about 65%. Various amounts of the formulated agents were suspended in water which additionally contained about 0.25% by weight of a surface-active agent (nonylphenol).

In each case 0.3 ml of the suspensions were administered by means of an injection into the spindle region at the height of the last visible dewlap (10 plants per concentration). The leaves were removed from the treated plants as well as from the untreated controls after 3 weeks, during harvesting, and the internodes were analyzed in groups to determine their sucrose content. The results are represented in Table 7.

TABLE 7

| Compound of Example | Concentration used (kg/hectare) | Sugar content (%) at harvesting |
|---|---|---|
| 56 | 0.62 | 164 |
| 31 | 0.62 | 181 |
| control |  | 100% |

Example V (Abscission effect in citrus plants)

Branch sections of orange-trees (species Hamlin, Pineapple and Valencia) carrying at least 20 fruits were sprayed with solutions of active ingredients shortly prior to harvesting. Evaluation was done 7 days later by measuring the retention of the fruits.

TABLE 8

| Ex. No | Dosage | Retention (kg) |
|---|---|---|
| control |  | 6.5 |
| 5-chloro-3-methyl-4-nitropyrazole (comparison) |  | 1.6 |
| 57 | 1,000 | 1.4 |
| 79 | 1,000 | 0 |
| 106 | 1,000 | 1.9 |

The aforesaid compounds exhibited an excellent compatibility with citrus trees.

They did not damage the leaves and immature fruits. In comparison to the technical standard, the substances resulted in far less significant injuries of the peel of mature fruits. As is known, an injury of the peel induces a release of ethylene by the wound upon application of citrus abscission agents, which promotes a development of the separation layer and results in a separation of the fruits.

We claim:

1. A compound of the formula

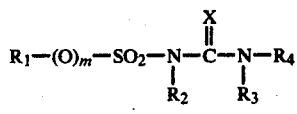

wherein $R_1$ is an alkyl, alkenyl or alkadienyl radical which has up to 10 C atoms, is optionally substituted by up to 6 halogen atoms, and can be interrupted by oxygen, $R_2$ and $R_3$ are H or $(C_1-C_4)$-alkyl, X is 0 or S, m is 0 or 1 and $R_4$ is a six-membered 1,3,5-triazine mono- or di-substituted by halogen, $NO_2$, CN, CHO, $(C_1-C_4)$-alkylamino, $(C_1-C_4)$-dialkylamino or a combination thereof; $(C_1-C_4)$-alkyl optionally substituted by halogen, $(C_1-C_3)$-alkoxy, $(C_1-C_3)$-alkylthio, $(C_1-C_3)$-alkylamino, $(C_1-C_3)$-dialkylamino, $(C_1-C_4)$-alkoxycarbonyl or a combination thereof; $(C_1-C_4)$-alkoxy or $(C_1-C_4)$-alkylthio optionally substituted by halogen, $(C_1-C_4)$-alkoxycarbonyl or a combination thereof; $(C_1-C_4)$-alkoxycarbonyl, or a combination thereof; and, if $R_2$ is hydrogen, a physiologically tolerated salt thereof with a base.

2. A herbicidal composition comprising a herbicidally effective concentration of a compound defined in claim 1 and an inert carrier material therefor.

3. A plant growth regulating composition comprising a concentration of a compound defined in claim 1 that is effective to regulate plant growth and an inert carrier material therefor.

4. A process for combatting undesired plant growth or for regulating plant growth which comprises applying to plants or to the situs of plants an effective concentration of a compound defined in claim 1.

5. A compound of the formula

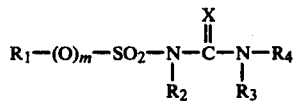

wherein $R_1$ is an alkyl, alkenyl or alkadienyl radical which has up to 10 C atoms, is optionally substituted by up to 6 halogen atoms, and can be interrupted by oxygen, $R_2$ and $R_3$ are H or $(C_1-C_4)$-alkyl, X is 0 or S, m is 0 or 1 and $R_4$ is six-membered 1,3,5-triazine disubstituted by $(C_1-C_4)$-dialkylamino, $(C_1-C_4)$-alkyl, $(C_1-C_4)$-alkoxy, $(C_1-C_4)$-alkylthio, $(C_1-C_4)$-alkoxycarbonyl or a combination thereof; and, if $R_2$ is hydrogen, a physiologically tolerated salt thereof with a base.

6. The compound of claim 5 which is N-(4-methoxy-6-methyl-1,3,5-triazin-2-yl)-N'-(threo-1,2-dichloro-n-prop-1-yl-sulfonyl)-urea.

7. The compound of claim 5 which is N-(4-methoxy-6-methyl-1,3,5-triazin-2-yl)-N'-(3-chloro-n-but-2-yl-sulfonyl)-urea.

8. The compound of claim 5 which is N-(4,6-dimethyl-1,3,5-triazin-2-yl)-N'-(but-2-en-2-yl-sulfonyl)-urea.

9. The compound of claim 5 which is the cis-isomer of N-(4-methoxy-6-methyl-1,3,5-triazin-2-yl)-N'-(but-2-en-2-yl-sulfonyl)-urea.

10. The compound of claim 5 which is the trans-isomer of N-(4-methoxy-6-methyl-1,3,5-triazin-2-yl)-N'-(but-2-en-2-yl-sulfonyl)-urea.

11. The compound of claim 5 which is the cis-isomer of N-(4-ethoxy-6-methyl-1,3,5-triazin-2-yl)-N'-(but-2-en-2-yl-sulfonyl)-urea.

12. The compound of claim 5 which is the trans-isomer of N-(4-ethoxy-6-methyl-1,3,5-triazin-2-yl)-N'-(but-2-en-2-yl-sulfonyl)-urea.

13. The compound of claim 5 which is N-(4-methoxy-6-methyl-1,3,5-triazin-2-yl)-N'-(1,2-dibromo-n-but-2-yl-sulfonyl)-urea.

* * * * *